United States Patent [19]

Katsunuma

[11] 4,297,347
[45] Oct. 27, 1981

[54] NUCLEOSIDE DERIVATIVES AND AN ANTILEUKEMIAL AGENT CONTAINING THE SAME AS AN ACTIVE INGREDIENT

[76] Inventor: Nobuhiko Katsunuma, No. 1-78, Shomachi, Tokushima-shi, Tokushima-ken, Japan

[21] Appl. No.: 89,887

[22] Filed: Oct. 31, 1979

[30] Foreign Application Priority Data

Oct. 31, 1978 [JP] Japan ................................ 53-134708
Jan. 11, 1979 [JP] Japan ..................................... 54-2564
Jan. 11, 1979 [JP] Japan ..................................... 54-2565

[51] Int. Cl.$^3$ ...................... A61K 31/70; C07H 19/20; C07H 19/10
[52] U.S. Cl. ...................................... 424/180; 536/28; 536/29

[58] Field of Search ....................... 536/23, 24, 28, 29; 424/180

[56] References Cited

U.S. PATENT DOCUMENTS

| | | | |
|---|---|---|---|
| 3,299,042 | 1/1967 | Lipkin .................................... | 536/23 |
| 3,382,233 | 5/1968 | Samejima et al. ..................... | 536/28 |
| 3,462,416 | 8/1969 | Hanze et al. ........................... | 536/23 |
| 3,475,409 | 10/1969 | Ouchi et al. ........................... | 536/28 |
| 3,830,798 | 8/1974 | Herndon et al. ....................... | 536/24 |
| 4,141,972 | 2/1979 | Nishino et al. ........................ | 536/28 |

*Primary Examiner*—Johnnie R. Brown
*Attorney, Agent, or Firm*—Browdy and Neimark

[57] ABSTRACT

A 3'-polyphosphate of pyrimidine nucleoside or guanosine or a pharmaceutically acceptable salt thereof which has high antileukemial activity and is low in toxicity is disclosed.

8 Claims, No Drawings

NUCLEOSIDE DERIVATIVES AND AN ANTILEUKEMIAL AGENT CONTAINING THE SAME AS AN ACTIVE INGREDIENT

This invention relates to nucleoside derivatives, especially 3'-polyphosphates of pyrimidine nucleoside and guanosine, and to an antileukemial agent containing such derivatives as an active ingredient.

Nucleosides occur in all living cells as a component of nucleic acid, and the nucleotide which is the class of esters formed by interacting nucleosides with phosphoric acid has been the subject of many studies conducted to date, but adenosine has been the only nucleoside from which 3'-polyphosphates (e.g. 3'-di or -tri-phosphate) of nucleosides can be synthesized.

The inventors of this invention have succeeded in preparing a novel nucleoside-3'-polyphosphate by first converting 3'-monophosphate of pyrimidine nucleoside or guanosine to the corresponding reactive derivative such as amidate or morpholidate in the conventional manner and esterifying the derivative with phosphoric acid. Subsequent to the success, the inventors have unexpectedly found that the polyphosphate has high antileukemial activity.

The term "pyrimidine nucleoside" as used herein means nucleosides including cytidine, uridine and thymidine. Illustrative nucleoside-3'-polyphosphates that are the end compound of this invention are uridine-3'-diphosphate, uridine-3'-triphosphate, cytidine-3'-diphosphate, cytidine-3'-triphosphate, guanosine-3'-diphosphate and guanosine-3'-triphosphate. These polyphosphates may be in the form of pharmaceutically acceptable salts of sodium, potassium, lithium, etc.

When the nucleoside-3'-polyphosphate of this invention is used as an anti-leukemial agent, it may be formulated in a form suitable for either oral aministration or injection. The forms suitable for oral administration include a tablet, granule, powder, suspension and lemonade, and the granule or powder may be encapsulated and administered as a capsule. The nucleoside-3'-polyphosphate of this invention may be formulated into a tablet, granule or powder by compounding it in the conventional manner with lactose, starch, dextrin, sucrose, crystalline cellulose, kaolin, calcium carbonate, talc and other substances conventionally used as a carrier for medicines. A suspension is prepared by suspending the active ingredient in an oily solvent such as corn oil and olive oil, and a lemonade is prepared by dissolving said active ingredient in an aqueous solution of citric acid, tartaric acid, etc. An injection is prepared by dissolving the nucleoside-3'-polyphosphate in an isotonic aqueous solution of sodium chloride, potassium chloride, etc., which is either placed in an ampoule followed by sealing, or placed in a vial followed by lyophilization.

When the nucleoside-3'-polyphosphate of this invention is formulated into an antileukemial composition, a single dose of each formulation or a dose unit may contain a sufficient amount of the polyphosphate to work effectively in treatment of certain forms of leukemia. A tablet, granule, powder, capsule, suspension and lemonade as a formulation for oral administration generally contains 10 to 5,000 mg, preferably from 50 to 500 mg, of the active ingredient per dose unit, whereas an injection generally contains 10 to 1,000 mg, preferably from 50 to 500 mg, of the active ingredient per dose unit.

The nucleoside-3'-polyphosphate of this invention is so low in human toxicity that more than a dose unit of the antileukemic composition described could be administered for treatment of leukemia, but from the viewpoint of safety and economy, the maximum dosage per day is preferably 300 mg/kg body weight for oral administration and 30 mg/kg body weight for injection.

The nucleoside-3'-polyphosphate has been shown effective as an anti-leukemic agent against L5178Y lymphatic leukemia in mice.

This invention is now described in greater detail by reference to the following working examples and experiments which are given here for illustrative purposes only and are by no means intended to limit the scope of this invention.

EXAMPLE 1

Three millimoles of guanosine-3'-monophosphate were dissolved in a mixture of 7.5 ml of 2 N ammonia water and 5 ml of formamide, the solution was combined with 20 ml of tertiary butanol that contained 15 millimoles of dicyclohexyl carbodiimide, and the resulting mixture was heated at 80° C. for a period of 9 to 10 hours with care taken to prevent evaporation of the solvent. After the reaction, the mixture was left to stand overnight at room temperature, the precipitate was filtered off, the filtrate was concentrated under vacuum to remove the tertiary butanol, and the residue was extracted with ether. The aqueous layer was recovered, concentrated under vacuum, and the residue was treated with acetone to give a crystal of guanosine-3'-monophosphoramidate in a yield of about 50%. The crystal was heated under vacuum at 100° C. for a period of 3 to 4 hours until it was dehydrated thoroughly.

A mixture of 0.35 millimoles of the guanosine-3'-monophosphoramidate and 1.5 millimoles of inorganic phosphoric acid was dissolved in 2.0 ml of dried pyridine, the solution was left to stand at room temperature for a period of 3 or 4 days, the undissolved matter was filtered off, and the filtrate was concentrated under vacuum to remove the pyridine. The residue was dissolved in 25 ml of an aqueous solution that contained 1 g of sodium acetate, the solution was adjusted to a pH of 7.0 with sodium hydroxide, and washed five times with ether twice the volume of the solution to remove the guanidium salt. The solution was then passed through a column of Dowex 2 (Cl⁻ type: manufactured by Dow Chemical Co.) to remove the unreacted guanosine-3'-monophosphoramidate. The solution was treated with lithium hydroxide to bring its pH to 6.5, concentrated under vacuum, the residue was dissolved in 25 ml of methanol, to which was added 200 ml of acetone to precipitate the crystal of a lithium salt of guanosine-3'-diphosphate. The crystal was passed through a column of Dowex 50 (H⁺ type) for desalting. The eluate was collected, concentrated under vacuum, and the residue was lyophilized to give guanosine-3'-diphosphate.

The U.V. absorption spectrum of the diphosphate had a peak at 256 nm and a shoulder at about 270 nm. Determination of guanine by the U.V. method, inorganic phosphate as formed by the hydrolysis with sulfuric acid and ribose by using the orcinol reaction and phenol-sulfuric acid reaction indicated that the diphosphate comprised guanine, inorganic phosphate and ribose in a ratio of about 1:2:1. When the diphosphate was subjected to the labile phosphate reaction using ammonium molybdate (Fick-Subbarow Method), it turned blue, suggesting that the two phosphate groups were directly linked with each other. Gel chromatography of the product on a silica gel plate using a developing agent comprising isopropanol, ammonia water and water (7:1:2) gave an Rf of 0.34. For the sake of comparison, the Rf levels of the following control compounds were determined under the same conditions as above:

Guanosine-3'-monophosphate: 0.40
Guanosine-5'-monophosphate: 0.17
Guanosine-5'-diphosphate: 0.05
Guanosine-5'-triphosphate: 0.03

EXAMPLE 2

Three millimoles of guanosine-3'-monophosphate were dissolved in 60 ml of 50% tertiary butanol that contained 12 millimoles of morpholine, and 45 ml of tertiary butanol containing 12 millimoles of dicyclohexylcarbodiimide was added dropwise to the solution under reflux with stirring. After the dropwise addition, the reaction was continued for 5 or more hours under reflux, and thereafter, it was cooled to room temperature, the precipitate was filtered off, the filtrate was concentrated under vacuum to remove the tertiary butanol, and the aqueous layer was washed with ethanol. The aqueous layer was concentrated under vacuum, and the residue was dissolved in a small amount of methanol, the undissolved matter was filtered off, and the filtrate was mixed with ethanol to give a 4-morpholine-N,N'-dicyclohexylcarboxamidine salt of guanosine-3'-phosphoromorpholidate in a yield of about 50%. The product was dried thoroughly by heating under vacuum at 100° C. for a period of 3 to 4 hours. A sixth of the dried product was mixed with 5 ml of pyridine, concentrated under vacuum to remove the moisture content, mixed with benzene and concentrated under vacuum to remove the pyridine.

One millimole of tetrasodium pyrophosphate decahydrate was dissolved in water, the solution was passed through a column of Dowex 50W (pyridinium type, volume: 15 ml) and eluted with water. The eluate was concentrated to about 10 ml, mixed with 30 ml of pyridine and 1 ml of tributylamine, and concentrated under vacuum. The residue was mixed with 10 ml of dried pyridine, concentrated under vacuum to remove the moisture content, mixed with dried benzene and concentrated under vacuum to remove the pyridine. The pyridine-free product was dissolved in 1 ml of dried dimethyl sulfoxide, the dried 4-morpholine-N,N'-dicyclohexylcarboxamidine salt of guanosine-3'-phosphoromorpholidate was added to the solution, and the mixture was left to stand at room temperature for a period of 4 days with the container stoppered. Thirty milliliters of water were added to the mixture, which was passed through a column of DEAE-cellulose (2×35 mm, hydrogen bicarbonate type) and eluted by the linear gradient of aqueous triethylammonium bicarbonate. Fractions containing guanosine-3'-triphosphate were collected and concentrated under vacuum. The residue was dissolved in methanol and concentrated under vacuum to remove the triethylammonium bicarbonate, and the residue was dissolved in 5 ml of ethanol, and mixed first with 1 M sodium iodide in acetone and then with 75 ml of acetone to give a tetrasodium salt of guanosine-3'-triphosphate.

The U.V. absorption spectrum of the salt had a peak at 256 nm and a shoulder at around 270 nm. Determination of guanine by the U.V. method, inorganic phosphate as formed by the hydrolysis with sulfuric acid and ribose by using the orcinol reaction and phenol-sulfuric acid reaction indicated that the salt comprised guanine, inorganic phosphate and ribose in a ratio of about 1:3:1. When the salt was subjected to the labile phosphate reaction using ammonium molybdate (Fisk-Subbarow Method), it turned blue, and two of the three phosphate groups were determined, thus suggesting that the three phosphate groups were directly linked with each other. Gel chromatography of the salt on a silica gel plate using a developing agent comprising isopropanol, ammonia water and water (7:1:2) gave an Rf of 0.20.

EXAMPLE 3

The procedure of Example 1 was repeated except that guanosine-3'-monophosphate was replaced by uridine-3'-monophosphate. The resulting product was uridine-3'-diphosphate.

The U.V. absorption spectrum of the diphosphate had a peak at 261 nm. Determination of uracil by the U.V. method, inorganic phosphate as formed by the hydrolysis with sulfuric acid, and ribose by using the phenol-sulfuric acid reaction indicated that the product comprised uracil, inorganic phosphate and ribose in a ratio of about 1:2:1. When the diphosphate was subjected to the labile phosphate reaction using ammonium molybdate (Fisk-Subbarow Method), it turned blue, suggesting that the two phosphate groups were directly linked with each other.

EXAMPLE 4

Cytidine-3'-diphosphate was prepared by repeating the procedure of Example 1 except that guanosine-3'-monophosphate was replaced by cytidine-3'-monophosphate.

The U.V. absorption spectrum of the diphosphate had a peak at 271 nm under both alkaline and neutral conditions, and at 279 nm under acidic condition. Determination of cytosine by the U.V. method, inorganic phosphate as formed by the hydrolysis with sulfuric acid, and ribose by using the phenol-sulfuric acid reaction indicated that the product comprised cytosine, ribose and inorganic phosphate in a ratio of about 1:1:2. When the product was subjected to the labile phosphate reaction using ammonium molybdate (Fisk-Subbarow Method), it turned blue, suggesting that the two phosphate groups were directly linked with each other. Gel chromatography on a silica gel using a developing agent comprising isopropanol, ammonia water and water (7:1:2) gave an Rf of 0.03.

EXAMPLE 5

Cytidine-3'-triphosphate was prepared by repeating the procedure of Example 2 except that guanosine-3'-monophosphate was replaced by cytidine-3'-monophosphate.

The U.V. absorption spectrum of the product had a peak at 271 nm under alkaline and neutral conditions, and at 279 nm under acidic condition. Determination of cytosine by the U.V. method, inorganic phosphate as formed by the hydrolysis with sulfuric acid and ribose by using the phenolsulfuric acid reaction indicated that the product comprised cytosine, inorganic phosphate and ribose in a ratio of about 1:3:1. When the product was subjected to the acid labile phosphate reaction using ammonium molybdate (Fisk-Subbarow Method), it turned blue and two of the three phosphate groups were determined, thus suggesting that the three groups were directly linked with each other. Gel chromatography on a silica gel plate using a developing agent comprising isopropanol, ammonia water and water (7:1:2) gave an Rf of 0.01.

EXAMPLE 6

Uridine-3'-triphosphate was prepared by repeating the procedure of Example 2 except that guanosine-3'-monophosphate was replaced by uridine-3'-monophosphate.

The U.V. absorption spectrum of the triphosphate had a peak at 261 nm. Determination of uracil by the U.V. method, inorganic phosphate as formed by the hydrolysis with sulfuric acid, and ribose by using the phenol-sulfuric acid reaction indicated that the product comprised uracil, inorganic phosphate and ribose in a ratio of about 1:3:1. When the product was subjected to the labile phosphate reaction using ammonium molybdate (Fisk-Subbarow Method), it turned blue and two of the phosphate groups were determined, thus suggesting that the three groups were directly linked with each other.

Experiment 1

The following experiment was conducted to demonstrate the antitumor activity of cytidine-3'-triphosphate.

Nine groups of male DBA/2 strain mice (each group consisting of 3 mice weighing 17 g on average) were inoculated with $4.2 \times 10^6$ L 5178Y lmyphatic leukemic cells/head in the inguinal region. On the 2nd day up to the 6th day of the inoculation, four groups were administered intraperitoneally cytidine-3'-triphosphate once a day, and other four groups were similarly administered triamcinolone. The last group was the control which was administered neither the triphosphate nor triamcinolone. On the 7th day of the inoculation, each mice was sacrificed and the tumor weight was measured to see the ability of each test compound to retard the growth of leukemic cells. The results are shown in Tables 1 and 2 below. As is clear from Table 1, the effect of triamcinolone did not appear before it was administered in a dose of 4.0 mg/kg and it was noticeable in the group administered 30 mg/kg of triamcinolone. On the other hand, as Table 2 demonstrates, the cytidine-3'-triphosphate exhibited the effect of inhibiting the growth of leukemic cells even when it was administered in an amount of 0.05 mg/kg, and considerable inhibition was observed in the group administered 1.0 mg/kg of the triphosphate. In the experiment, the mice of the group administered 4.0 mg/kg of triamcinolone weighed about 20% less than the control, and this percentage increased as more triamcinolone was administered. In contrast, the groups administered cytidine-3'-triphosphate gained as much weight as the control, while the triphosphate exhibited a high anti-tumor activity as demonstrated in Table 2, thus evidencing its great safety as a pharmaceutical agent.

TABLE 1

| dose of triamcinolone (mg/kg body weight) | tumor weight (mg ± SE) |
| --- | --- |
| 0 (control) | 763.0 ± 51.0 |
| 1.0 | 754.7 ± 95.2 |
| 4.0 | 398.0 ± 26.3 P <0.01 |
| 15.0 | 310.9 ± 45.0 P <0.01 |

TABLE 1-continued

| dose of triamcinolone (mg/kg body weight) | tumor weight (mg ± SE) |
| --- | --- |
| 30.0 | 29.3 ± 12.6 P <0.001 |

TABLE 2

| dose of cytidine-3'-triphosphate (mg/kg body weight) | tumor weight (mg ± SE) |
| --- | --- |
| 0 (control) | 763.0 ± 51.0 |
| 0.05 | 175.6 ± 71.8 P <0.01 |
| 0.2 | 196.5 ± 93.9 P <0.01 |
| 1.0 | 41.5 ± 12.1 P <0.001 |
| 4.0 | 39.5 ± 23.2 P <0.001 |

Experiment 2

The procedure of Experiment 1 was repeated to evaluate the activity of guanosine-3'-diphosphate and guanosine-3'-triphosphate as an agent for inhibiting the growth of leukemic cells. The results are shown in Tables 3 and 4 below.

TABLE 3

| dose of guanosine-3'-diphosphate (mg/kg body weight) | tumor weight (mg ± SE) |
| --- | --- |
| 0 (control) | 756.0 ± 47.0 |
| 0.05 | 174.7 ± 72.6 P <0.01 |
| 0.2 | 240.3 ± 88.8 P <0.01 |
| 1.0 | 43.0 ± 14.6 P <0.001 |
| 4.0 | 67.0 ± 53.2 P <0.001 |

TABLE 4

| dose of guanosine-3'-triphosphate (mg/kg body weight) | tumor weight (mg ± SE) |
| --- | --- |
| 0 (control) | 781.2 ± 53.6 |
| 0.05 | 170.9 ± 70.4 P <0.01 |
| 0.2 | 165.0 ± 81.3 P <0.01 |
| 1.0 | 39.6 ± 15.5 P <0.001 |
| 4.0 | 41.6 ± 32.0 P <0.001 |

What is claimed is:

1. A compound selected from the group consisting of guanosine-3'-diphosphate, guanosine-3'-triphosphate, uridine-3'-diphosphate, uridine-3'-triphosphate, cytidine-3'-diphosphate, cytidine-3'-triphosphate, and a pharmaceutically acceptable salt thereof.

2. Guanosine-3'-diphosphate or a pharmaceutically acceptable salt thereof according to claim 1.

3. Guanosine-3'-triphosphate or a pharmaceutically acceptable salt thereof according to claim 1.

4. Uridine-3'-diphosphate or a pharmaceutically acceptable salt thereof according to claim 1.

5. Uridine-3'-triphosphate or a pharmaceutically acceptable salt thereof according to claim 1.

6. Cytidine-3'-diphosphate or a pharmaceutically acceptable salt thereof according to claim 1.

7. Cytidine-3'-triphosphate or a pharmaceutically acceptable salt thereof according to claim 1.

8. An agent effective against L5178Y lymphatic leukemia in mice containing a pharmaceutically acceptable carrier and a pharmaceutically acceptable amount of a compound in accordance with claim 1.

* * * * *